(12) United States Patent
Guo et al.

(10) Patent No.: US 12,420,302 B2
(45) Date of Patent: Sep. 23, 2025

(54) ULTRASONIC ELECTRONIC CIGARETTE ATOMIZER

(71) Applicant: CHINA TOBACCO HUNAN INDUSTRIAL CO., LTD., Hunan (CN)

(72) Inventors: Xiaoyi Guo, Hunan (CN); Wei Huang, Hunan (CN); Hong Yu, Hunan (CN); Yuangang Dai, Hunan (CN); Xinqiang Yin, Hunan (CN); Jianhua Yi, Hunan (CN); Kejun Zhong, Hunan (CN); Jianfu Liu, Hunan (CN); Youlin He, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 0 days.

(21) Appl. No.: 18/231,036

(22) Filed: Aug. 7, 2023

(65) Prior Publication Data
US 2023/0372961 A1    Nov. 23, 2023

Related U.S. Application Data

(62) Division of application No. 16/337,291, filed as application No. PCT/CN2017/073780 on Feb. 16, 2017, now Pat. No. 11,759,817.

(30) Foreign Application Priority Data

Sep. 30, 2016    (CN) .......................... 201621099688.4
Oct. 12, 2016    (CN) .......................... 201621116306.4

(51) Int. Cl.
A24F 40/46    (2020.01)
A24F 40/05    (2020.01)
(Continued)

(52) U.S. Cl.
CPC .......... *B05B 17/0607* (2013.01); *A24F 40/05* (2020.01); *A24F 40/44* (2020.01);
(Continued)

(58) Field of Classification Search
CPC .......... A24F 40/10; A24F 40/44; A24F 40/46
See application file for complete search history.

(56) References Cited

U.S. PATENT DOCUMENTS 9,055,617 B2    6/2015   Thorens et al.
9,078,475 B2    7/2015   Li et al.
(Continued)

FOREIGN PATENT DOCUMENTS

CN    205030516 U    2/2016
CN    205432146 U    8/2016

OTHER PUBLICATIONS

International Search Report, International Application No. PCT/CN2017/073780, mailed Jul. 5, 2017, 4 pages.

*Primary Examiner* — Russell E Sparks
(74) *Attorney, Agent, or Firm* — MASCHOFF BRENNAN; Elaine Lee; Michael Mauriel

(57) ABSTRACT

Disclosed is an ultrasonic electronic cigarette atomizer. An atomizer shell, an atomization piece and a liquid guide structure are arranged in the atomizer. The liquid guide structure communicates with a liquid storage cavity in the atomizer shell. A heating body is further arranged in the atomizer shell. Both of the atomization piece and the heating body are in contact with the liquid guide structure, and both of the heating body and an atomization surface of the atomization piece communicate with an airflow passage, and a positive electrode and a negative electrode of the heating body are respectively connected with one end and the other end of a power supply. The heating body can not only quickly heat the tobacco tar to approach to its atomization temperature, but also can transfer a part of heat to the (Continued)

atomization piece, so that the atomization piece atomizes the tobacco tar quickly, shortening the atomization time.

10 Claims, 13 Drawing Sheets

(51) Int. Cl.
*A24F 40/10* (2020.01)
*A24F 40/44* (2020.01)
*A24F 40/485* (2020.01)
*A61M 15/06* (2006.01)
*B05B 17/06* (2006.01)
*A24F 15/015* (2020.01)

(52) U.S. Cl.
CPC ............ *A24F 40/46* (2020.01); *A24F 40/485* (2020.01); *A61M 15/06* (2013.01); *A24F 15/015* (2020.01); *A24F 40/10* (2020.01)

(56) References Cited

U.S. PATENT DOCUMENTS

| | | | |
|---|---|---|---|
| 9,351,522 B2* | 5/2016 | Safari | A24F 40/44 |
| 9,622,511 B2* | 4/2017 | Zhu | A24F 40/42 |
| 9,675,107 B2 | 6/2017 | Levitz et al. | |
| 9,867,398 B2* | 1/2018 | Guo | B05B 17/0615 |
| 10,004,275 B2 | 6/2018 | Li et al. | |
| 10,660,367 B2 | 5/2020 | Li et al. | |
| 11,759,817 B2* | 9/2023 | Guo | A24F 40/46 |
| | | | 131/329 |
| 2016/0095352 A1* | 4/2016 | Liu | H01M 50/528 |
| | | | 429/65 |
| 2016/0338407 A1* | 11/2016 | Kerdemelidis | A24F 40/60 |

* cited by examiner

ULTRASONIC ELECTRONIC CIGARETTE ATOMIZER

CROSS REFERENCE TO RELATED APPLICATIONS

This application is a divisional of U.S. application Ser. No. 16/337,291 filed Mar. 27, 2019, which is a national phase application of international application number PCT/CN2017/073780 filed on Feb. 16, 2017, which claims priority to Chinese application number 201621116306.4 filed on Oct. 12, 2016, and Chinese application number 201621099688.4 filed on Sep. 30, 2016. The entire contents of these applications are hereby incorporated herein by reference.

TECHNICAL FIELD

The present invention belongs to the technical field of electronic cigarettes, and particularly relates to an ultrasonic electronic cigarette atomizer.

BACKGROUND ART

The existing ultrasonic electronic cigarette atomizer comprises an atomizer shell, a suction nozzle connected with the top end of the side wall of the atomizer shell, and an atomization piece, a liquid guide structure and a tobacco tar storage cavity in the atomizer shell, the liquid guide structure communicates with the tobacco tar storage cavity, and the liquid guide structure is in contact with one side surface of the atomization piece and is used for guiding tobacco tar to the surface of the atomization piece for atomization.

The existing ultrasonic electronic cigarette atomizer has the following disadvantages:

Firstly, it takes some time for the atomization piece to rise from the normal temperature to the working temperature, namely the atomization piece cannot immediately atomize the tobacco tar to produce smoke after being electrified, therefore the smoke of an electronic cigarette is insufficient at the beginning of use, a smoker cannot inhale the smoke or can only inhale a small amount of smoke for the previous puffs, and thus the user experience is poor.

Secondly, the structural design is unreasonable, the number of hollow cavities in the atomizer shell is small, and the volume of the hollow cavity is small, therefore the high temperature produced by the atomization piece at work is transferred to the atomizer shell easily, such that the surface of the atomizer shell becomes burning hot, resulting in discomfort of the user during hand holding.

Contents of Invention

The existing electronic cigarette atomizer lacks smoke at the beginning of use, and meanwhile an atomizer shell is liable to become burning hot, therefore the user experience is poor. The objective of the present invention is to provide an improved ultrasonic electronic cigarette atomizer in view of the above shortcomings of the prior art, in which the atomization speed is high, a larger amount of smoke can be obtained at the beginning of inhalation, the temperature of the atomizer shell is low, and user's comfort when inhaling is high.

In order to solve the above-mentioned technical problems, the technical solution adopted by the present invention is as follows:

An ultrasonic electronic cigarette atomizer comprises an atomizer shell, and an atomization piece and a liquid guide structure are arranged in the atomizer shell; the liquid guide structure communicates with a liquid storage cavity in the atomizer shell; the ultrasonic electronic cigarette atomizer is structurally characterized in that a heating body is further arranged in the atomizer shell, both of the atomization piece and the heating body are in contact with the liquid guide structure, and both of the heating body and an atomization surface of the atomization piece communicate with an airflow passage, and a positive electrode and a negative electrode of the heating body are respectively connected with one end and the other end of a power supply.

By means of the above structure, the heating body serves as an auxiliary heating structure and can perform auxiliary heating on tobacco tar on atomization cotton or heat the atomization piece, thereby increasing the temperature rise speed of the tobacco tar or the working temperature rise speed of the atomization piece, accordingly the electronic cigarette can atomize the tobacco tar at the beginning of work so as to produce smoke, the problem in the prior art that the smoke cannot be produced when the atomization piece is started up is solved, and the user experience is good. Meanwhile, the heating body can also directly heat the tobacco tar until the smoke is produced, thereby increasing the amount of smoke. Moreover, as the temperature of the tobacco tar on the atomization cotton is relatively high, the flow speed of the tobacco tar is relatively high, therefore sufficient supply of the tobacco tar during atomization can be guaranteed, and the dry burning problem caused by insufficient supply of the tobacco tar is avoided.

As a preferred mode, the liquid guide structure comprises atomization cotton in contact with one side surface of the atomization piece, both of the atomization piece and the atomization cotton are fixed on an atomization core bracket, and the atomization cotton is clamped between the heating body and the atomization piece.

Further, one end of the side wall of the atomizer shell is connected with a suction nozzle, a washer and a pressing ring, which are detachably connected with each other, are arranged in the atomization core bracket, the atomization cotton is of a flaky structure, and the atomization piece is arranged to be parallel to the length direction of an electronic cigarette; the atomization piece is fixed in the washer, one end of the atomization cotton is arranged between the washer and the pressing ring, and the other end of the atomization cotton extends into a tobacco tar bottle; a projection which abuts against the heating body is arranged on the pressing ring; a first hollow cavity which communicates with the suction nozzle is formed between the pressing ring and the atomization cotton; an air pass groove which communicates with the outside and is parallel to the length direction of the electronic cigarette is formed in the side wall, away from the atomization piece, of the pressing ring, an air pass hole is formed in a position in a position in the pressing ring, the position in the pressing ring corresponds to one end, away from the suction nozzle, of the atomization piece, and the air pass hole communicates the air pass groove and the first hollow cavity.

As the air pass groove is formed, when an atomization core is placed in the atomizer shell for use, a third hollow cavity for heat insulation is formed between the pressing ring and the side wall of the atomizer shell, therefore the temperature produced by the atomization piece at work is unlikely to be transferred to the atomizer shell through the pressing ring, thereby reducing the working temperature on the surface of the atomizer shell. As the air pass groove communicates with the suction nozzle, the internal heat can be taken out by the airflow in time, thereby further reducing the working temperature on the surface of the atomizer shell.

A depressed region is formed in the outer side wall of the atomization core bracket.

By means of the above structure, when the atomization core is placed in the atomizer shell for use, a fourth hollow cavity for heat insulation is formed between the atomization core bracket and the side wall of the atomizer shell, therefore the temperature produced by the atomization piece at work is unlikely to be transferred to the atomizer shell through the atomization core bracket, thereby reducing the working temperature on the surface of the atomizer shell.

Further, a second hollow cavity is formed between the atomization piece and the washer.

Due to the arrangement of the second hollow cavity, the temperature produced by the atomization piece at work is unlikely to be transferred to the atomizer shell through the washer and the atomization core bracket, thereby reducing the working temperature on the surface of the atomizer shell.

Further, a tobacco tar bottle placing cavity which places the tobacco tar bottle is formed in one end, away from the suction nozzle, of the atomization core bracket.

By means of the above structure, the tobacco tar bottle is embedded in the atomization core bracket to form an integrated structure so as to facilitate the production and assembly.

As a preferred mode, the heating body is in contact with a position, aligned to the central area of the atomization piece, of the atomization cotton, or the heating body is in contact with a position, close to a tobacco tar cup, of the atomization cotton.

If the heating body is in contact with the position, close to the tobacco tar cup, of the atomization cotton, namely the heating body is in contact with the position where the atomization cotton just comes out from the tobacco tar bottle, more tobacco tar can flow more quickly.

As a preferred mode, the heating body is an electric heating piece or a disc-shaped electric heating wire.

Further, a wiring groove is formed in the atomization core bracket.

During production, electronic wires run through wiring grooves so as to guarantee that the electronic wires will not be broken during the production to cause a short circuit phenomenon. Meanwhile, as the wiring grooves are embedded in the atomization core bracket, an integrated structure is formed to facilitate the production and assembly.

Further, a sealing pad is arranged in the suction nozzle.

The sealing pad is embedded in the suction nozzle so as to guarantee that an air inlet passage and an air outlet passage will produce no gas leakage phenomenon at work.

As another preferred mode, the heating body is arranged on the surface of the atomization piece and is in contact with the atomization piece.

As a preferred mode, the atomization piece, the heating body and the liquid storage cavity are sequentially arranged along outflow direction of the atomized gas.

The liquid storage cavity is formed above the atomization piece, therefore it is more convenient to enable the tobacco tar in the liquid storage cavity to flow onto the liquid guide structure.

As a preferred mode, the airflow passage comprises an air inlet pipe arranged in the liquid storage cavity and an air outlet pipe arranged in the air inlet pipe, the air inlet passage is arranged between the inner wall of the air inlet pipe and the outer wall of the air outlet pipe; the bottom end of the air outlet pipe communicates with upper surface of the heating body; the top end of the air outlet pipe is fixedly connected with a suction nozzle seat, and the air outlet pipe communicates with the suction nozzle on the suction nozzle seat; an air inlet hole is formed in the suction nozzle seat; and the air inlet passage communicates with the air inlet hole.

The airflow passage can guarantee that the external air enters the air inlet passage from an air inlet, and then mixed with the smoke atomized by the atomization piece at the bottom end of the air inlet passage, and then conveyed into the oral cavity of the user through the air outlet pipe and the suction nozzle, thereby being simple in structure and convenient to manufacture.

Further, the liquid guide structure is in contact with the upper surface of the heating body; the bottom end of the air inlet pipe abuts against (i.e., contact in a pressure state) the upper surface of the liquid guide structure through an adjusting mechanism which controls the throughput of the tobacco tar, and an air inlet notch is formed in the bottom end of the air outlet pipe; the air outlet passage is arranged in the air outlet pipe; and the air inlet passage communicates with the air outlet passage through the air inlet notch.

By means of the above structure, it can be guaranteed that the external air enters the air outlet pipe to take away the smoke in time so as to prevent the smoke from entering the air inlet passage to affect the taste of the smoke or cause a condensed tobacco tar accumulation phenomenon.

As a preferred mode, the adjusting mechanism comprises an elastic adjusting sleeve and a top seat; the upper end of the elastic adjusting sleeve is arranged between the air inlet pipe and the liquid storage cavity, and the bottom end of the air inlet pipe is in contact with the elastic adjusting sleeve; at least one liquid supply hole which communicates with the liquid guide structure is formed in the upper end of the elastic adjusting sleeve; the atomization piece, the heating body and the liquid guide structure are all provided in the inside of the lower end of the elastic adjusting sleeve; and the inner wall of the top seat is in threaded connection with the air inlet pipe.

The air inlet pipe can be rotated by the top seat, so the air inlet pipe produces an axial displacement to compress the elastic adjusting sleeve so as to control the pressing force applied to the liquid guide structure by the bottom of the air inlet pipe, thus the throughput of the tobacco tar can be controlled to prevent excessive tobacco tar from being soaked on the surface of the atomization piece to affect the atomization effect. Meanwhile, the elastic adjusting sleeve can relieve or isolate the high temperature produced in an atomization process from being transferred to the air inlet pipe so as to prevent the air inlet pipe from transferring the heat to the atomizer shell to avoid the phenomenon that the atomizer becomes burning hot.

As a preferred mode, the liquid guide structure comprises porous material; the liquid supply hole is covered by or filled with the upper surface of the porous material; and both of the liquid storage cavity and the elastic adjusting sleeve are arranged in the atomizer shell.

The elastic adjusting sleeve can seal and fix the atomization piece to prevent the leakage of the tobacco tar, and meanwhile the phenomenon that the atomization piece is stuck and cannot vibrate can be prevented.

As a preferred mode, the heating body is a heating wire or heating piece, the heating wire or the heating piece is embedded on the upper surface of the atomization piece; or the heating body is a netlike heating wire, and the netlike heating wire is superposed on the upper surface of the atomization piece.

The heating body and the atomization piece can be an integrated structure and can also be a superposed structure, thereby being simple to manufacture.

Further, the lower surface of the atomization piece is in contact with a plurality of elastic ejector pins; the elastic ejector pins are fixedly connected with an atomization bottom seat; and the lower end of the elastic adjusting sleeve is arranged in the atomization bottom seat.

The elastic ejector pins can ensure more stable and reliable internal electrical connection of the atomizer, compared with the electric conduction mode of electronic wires, the elastic ejector pins can prevent the high temperature produced by the atomization piece at work from melting a bonding pad to cause drop of the electronic wires and produce an open circuit phenomenon.

Further, an adjusting device which adjusts the airflow volumes of the air inlet hole is arranged on the suction nozzle seat.

The air inlet volume of the air inlet can be adjusted by the adjusting device, therefore the taste of the atomized gas can be improved.

Further, a tobacco tar injection opening is formed in the liquid storage cavity.

When there is no tobacco tar in the liquid storage cavity, the tobacco tar can be conveniently supplemented through the tobacco tar injection opening.

Compared with the prior art, the heating body of the present invention can not only quickly heat the tobacco tar to approach to its atomization temperature, but also can transfer a part of heat to the atomization piece, so that the atomization piece quickly starts to atomize the tobacco tar, therefore the atomization starting time is shortened, the atomization efficiency is high, the amount of smoke is large, the atomizer will not become burning hot, energy is saved, the user can obtain a larger amount of smoke at the beginning of smoking, the temperature of the atomizer shell is low, the atomization taste is purer, no burnt flavor is produced, and no hazardous substance will be produced by heating tobacco tar guide cotton, fibers or other tobacco tar guide materials; the structure is simple and ingenious, and the manufacture and use are convenient; and no pinhole needs to be provided in the atomization piece of the present invention to eject the atomized smoke, therefore the situation that the atomized smoke cannot be ejected when the gas is atomized because larger liquid molecules block the pinhole will not occur, and meanwhile the tobacco tar leakage of the atomizer can be better prevented.

Figure 1:
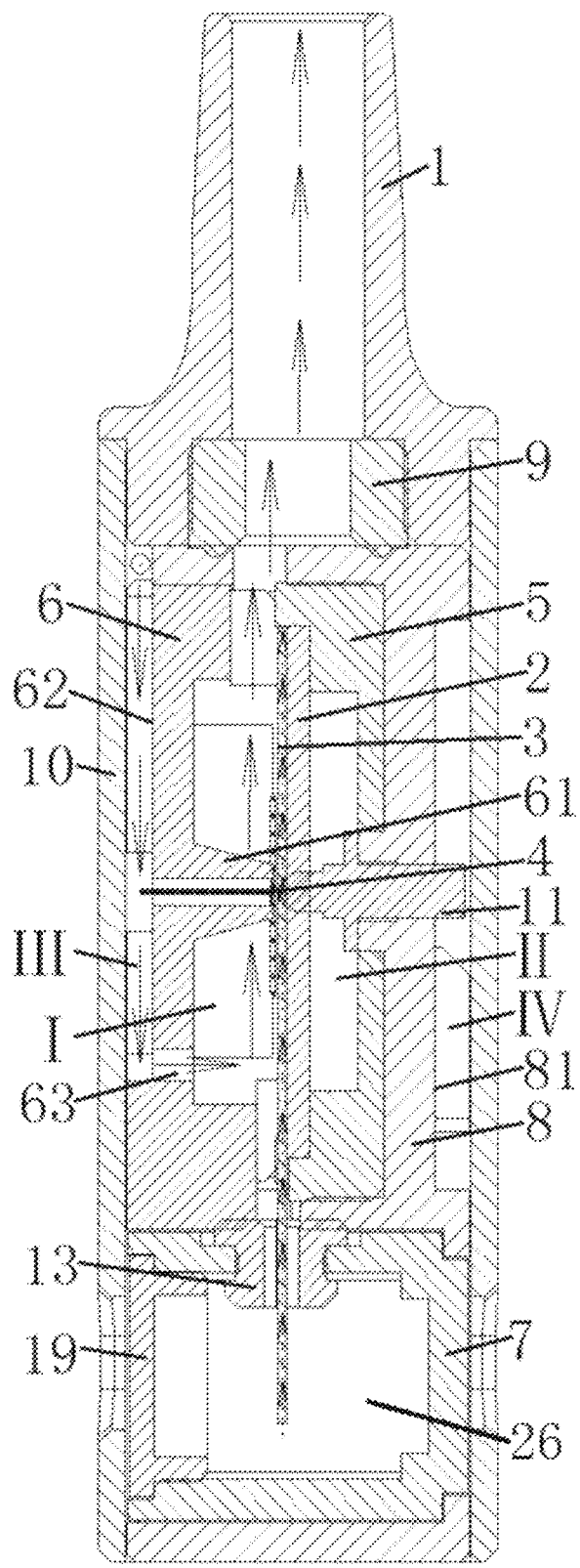
FIG. 1 is a front section view of an embodiment 1 of the present invention.
Figure 2:
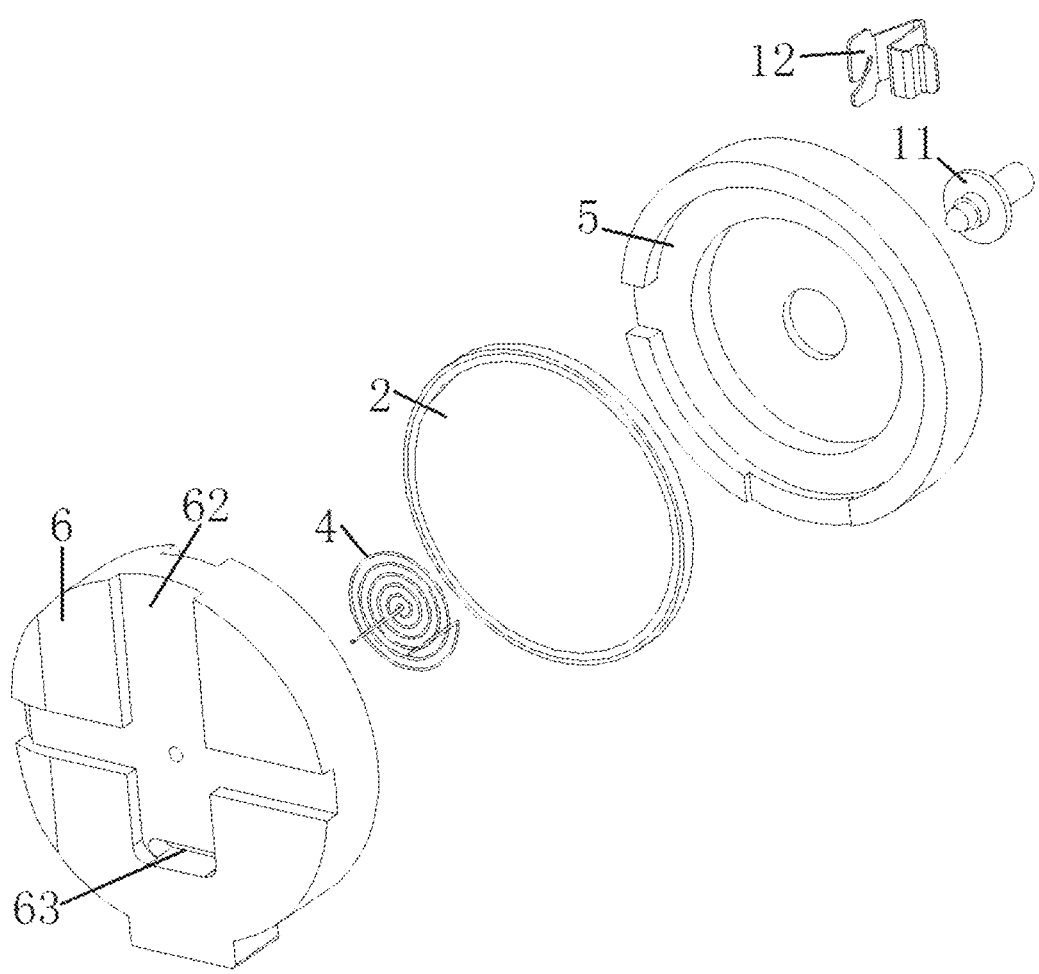
FIG. 2 is the left half part of an explosive view of FIG. 1.
Figure 3:
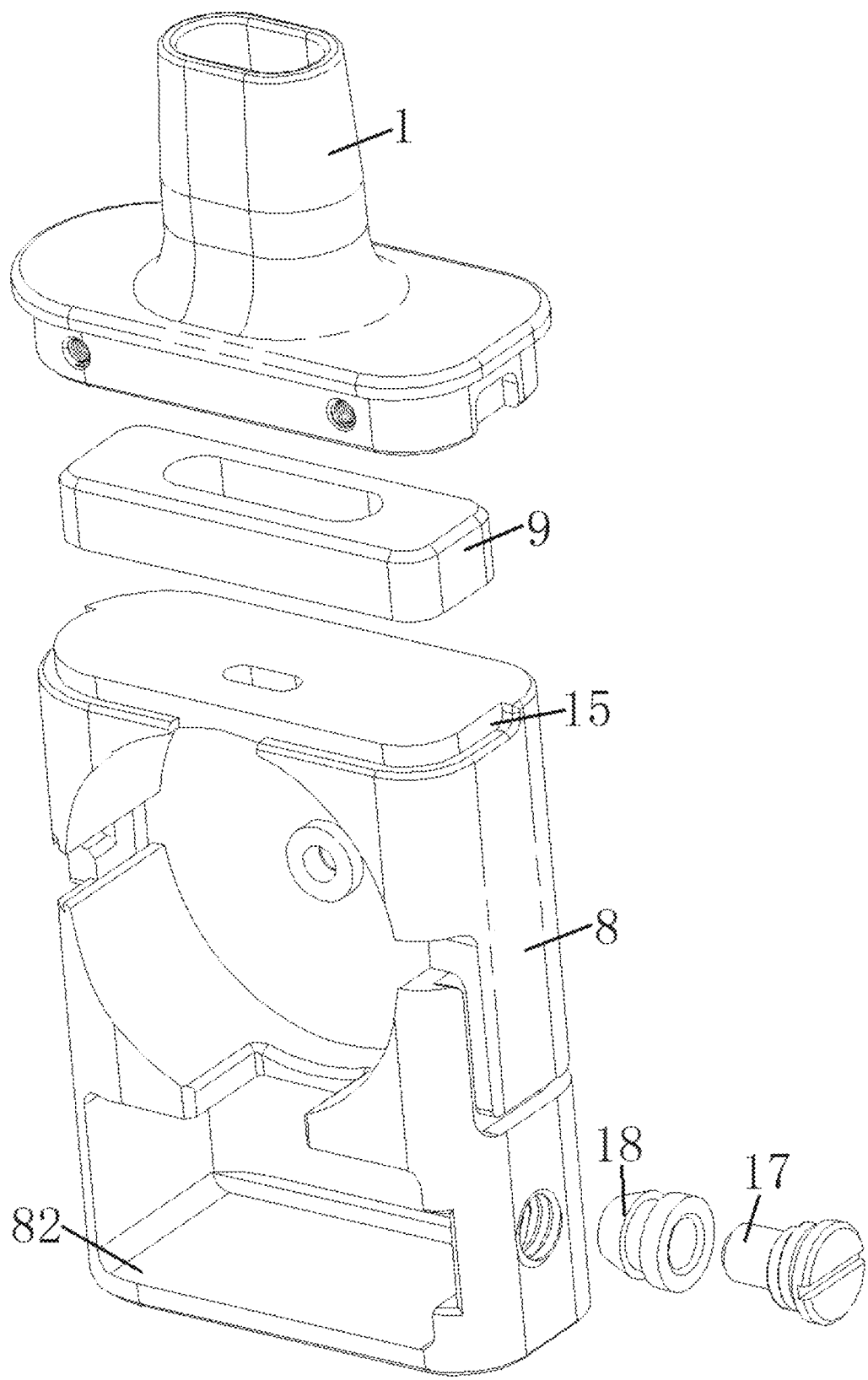
FIG. 3 is the upper right part of the explosive view of FIG. 1.
Figure 4:
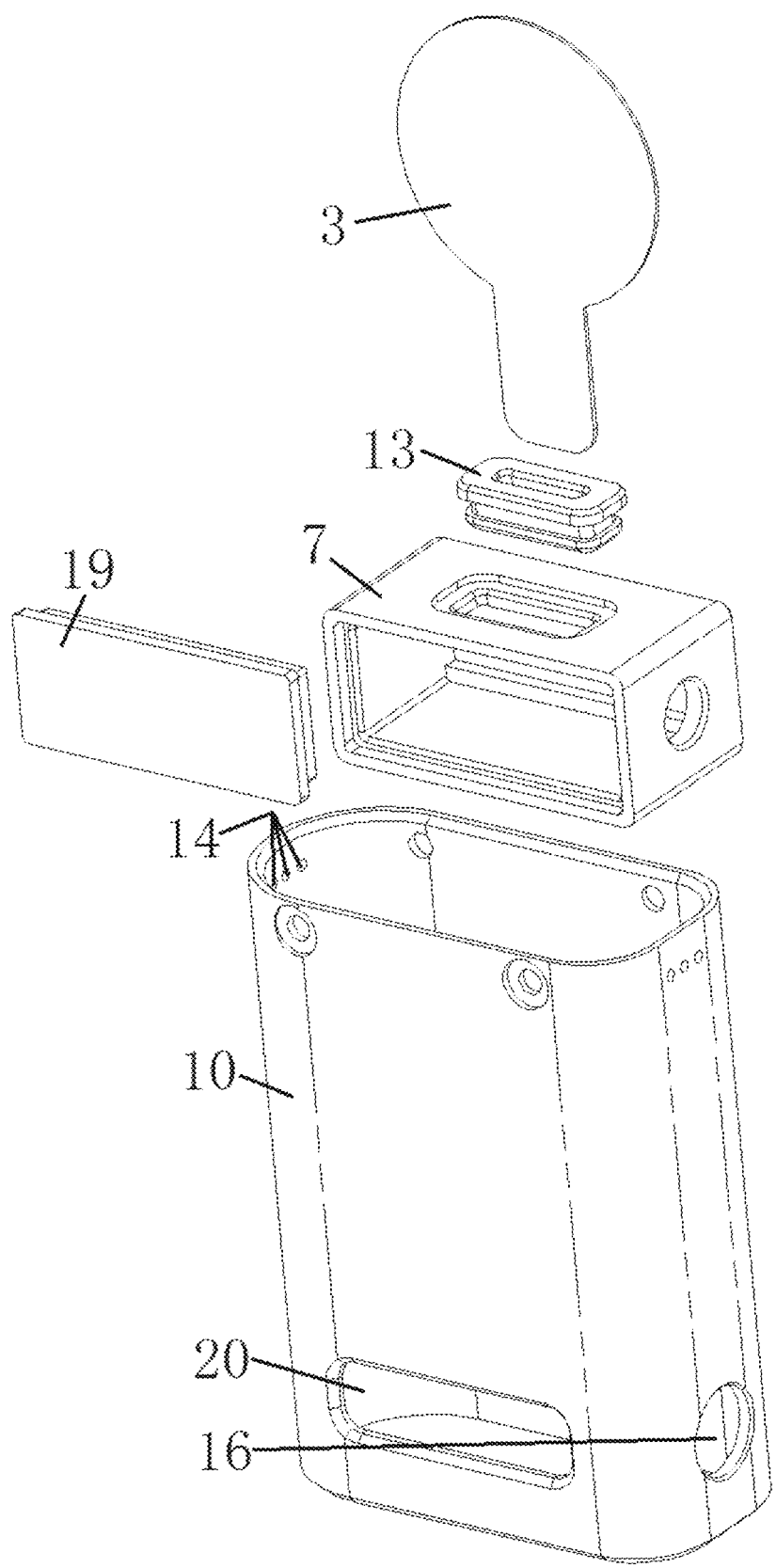
FIG. 4 is the lower right part of the explosive view of FIG. 1.
Figure 5:
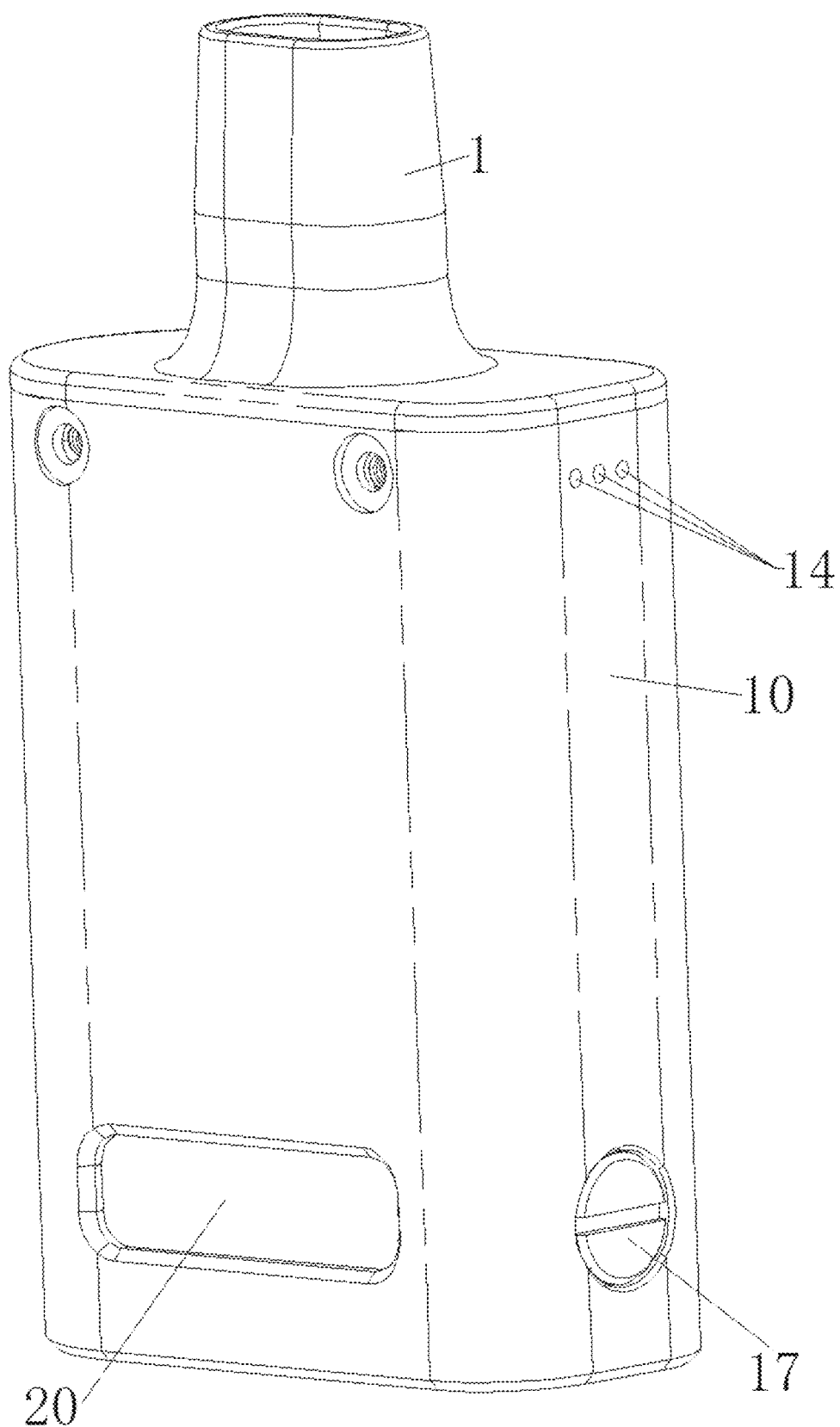
FIG. 5 is an appearance view of FIG. 1.

Reference signs: 1—suction nozzle, 2—atomization piece, 2A—first conducting layer, 2B—second conducting layer, 3 atomization cotton, 4—heating body, 5—washer, 6—pressing ring, 61—projection, 62—air pass groove, 63—air pass hole, 64—first through hole, 65—second through hole, 7—tobacco tar bottle, 8—atomization core bracket, 81—depressed region, 82—tobacco tar bottle placing cavity, 83—wiring groove, 9—sealing pad, 10—atomizer shell, 11—conductive terminal, 12—conductive contact plate, 13—tobacco tar guide sealing pad, 14—air inlet hole, 15—air inlet groove, 16—tobacco tar injection opening, 17—tobacco tar injection plug, 18—sealing ring, 19—tobacco tar bottle cover, 20—tobacco tar observation window, 21—liquid supply hole, 22—bottom seat, 23—atomization bottom seat, 24—atomization electrode, 25—electrode ring, 26—liquid storage cavity, 27—adjusting device, 28—atomization insulating ring, 29—piezoelectric ceramic layer, 30—bottom seat insulating ring, 31—air inlet pipe, 32—air outlet pipe, 321—air outlet passage, 33—air inlet passage, 34—air inlet notch, 35—suction nozzle seat, 36—glass outer wall, 37—porous material, 38—elastic adjusting sleeve, 101—elastic ejector pin, 102—top seat, I—first hollow cavity, II—second hollow cavity, III—third hollow cavity and IV—fourth hollow cavity.

SPECIFIC MODE FOR CARRYING OUT THE INVENTION

Embodiment 1

As shown in FIG. 1 to FIG. 6, an ultrasonic electronic cigarette atomizer in the embodiment 1 comprises an atomizer shell 10, and an atomization piece 2 and a liquid guide structure are arranged in the atomizer shell 10; the liquid guide structure communicates with a liquid storage cavity 26 in the atomizer shell 10; a heating body 4 is further arranged in the atomizer shell 10, both of the atomization piece 2 and the heating body 4 are in contact with the liquid guide structure, and both of the heating body 4 and an atomization surface of the atomization piece 2 communicate with an airflow passage, and a positive electrode and a negative electrode of the heating body 4 are respectively connected with one end and the other end of a power supply (the power supply is not shown in the drawings, but it does not affect understanding and implementation of the present invention by those skilled in the art).

The liquid guide structure comprises atomization cotton 3 which is in contact with one side surface of the atomization piece 2, both of the atomization piece 2 and the atomization cotton 3 are fixed on an atomization core bracket 8, and the atomization cotton 3 is clamped between the heating body 4 and the atomization piece 2.

One end of the side wall of the atomizer shell 10 is connected with a suction nozzle 1, and an ultrasonic electronic cigarette atomization core is arranged in the atomizer shell 10.

The atomization piece 2 is a solid piezoelectric ceramic piece. A conductive terminal 11 and a conductive contact plate 12 are arranged on the atomization core bracket 8 and are respectively in contact with the positive electrode and the negative electrode of the atomization piece 2, so as to guarantee the supply of electric energy necessary for atomization.

Figure 6:
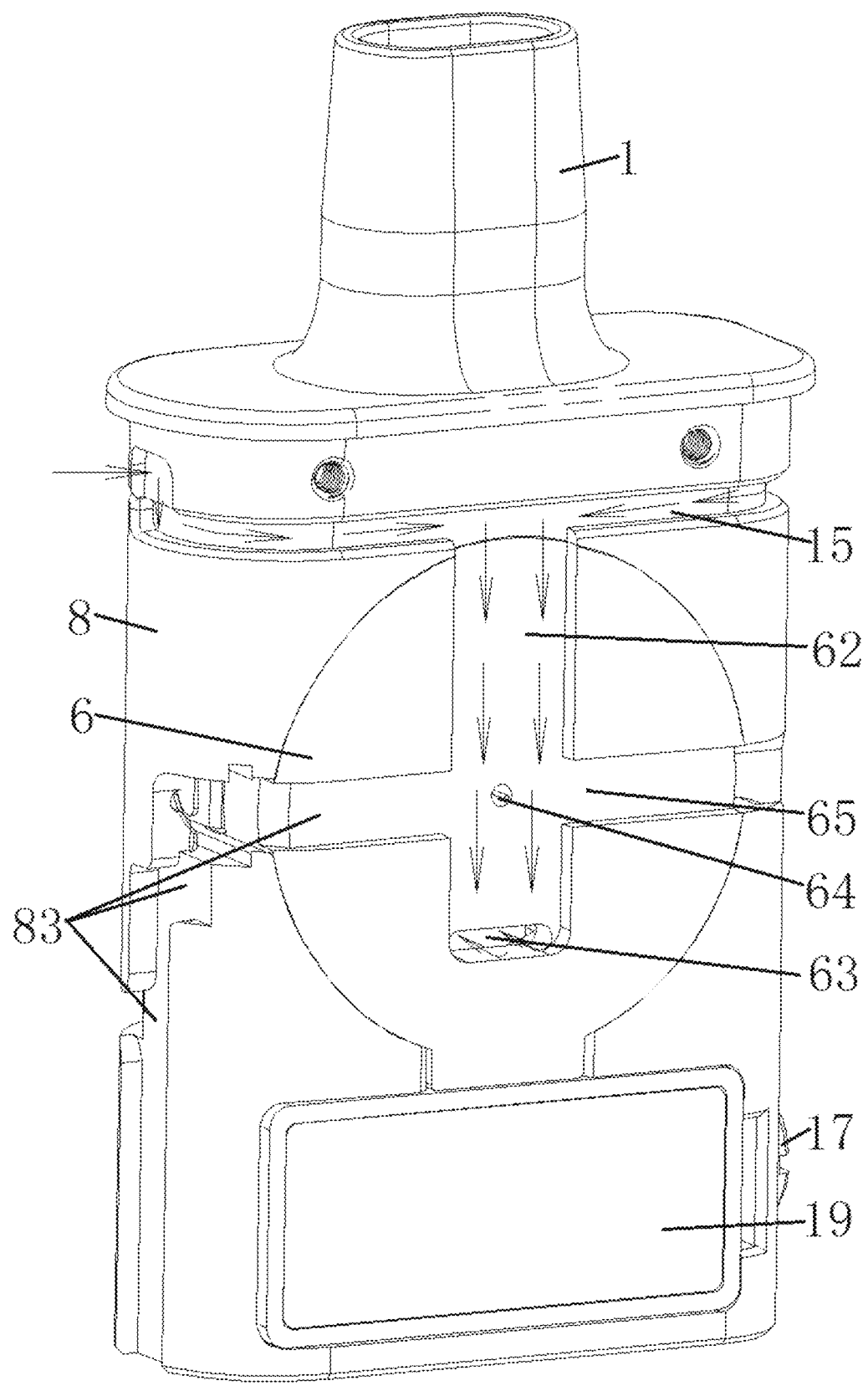
FIG. 6 is a structural schematic diagram after an atomizer shell is removed in FIG. 5.

A washer 5 and a pressing ring 6, which are detachably connected with each other, are arranged in the atomization core bracket 8, the atomization cotton 3 is of a flaky structure, and the atomization piece 2 is arranged to be parallel to the length direction of an electronic cigarette; the atomization piece 2 is fixed in the washer 5, one end of the atomization cotton 3 is arranged between the washer 5 and the pressing ring 6, and the other end of the atomization cotton 3 extends into a tobacco tar bottle 7. The direction as shown by a dotted arrow in FIG. 1 is a tobacco tar flow direction. A tobacco tar guide sealing pad 13 is arranged between the side wall of the tobacco tar bottle 7 and the atomization cotton 3. The atomization cotton 3 is of a porous structure and is made of an oleophylic material, the atomization cotton 3 transfers the tobacco tar which is at the bottom in the tobacco tar bottle 7 to the surface of the atomization piece 2 to be atomized and effectively provides the amount of tobacco leaves necessary for atomization for the atomization piece 2. A projection 61 which abuts against the heating body 4 is arranged on the pressing ring 6; a first hollow cavity I which communicates with the suction nozzle 1 is formed between the pressing ring 6 and the atomization cotton 3; an air pass groove 62 which communicates with the outside and is parallel to the length direction of the electronic cigarette is formed in the side wall, away from the atomization piece 2, of the pressing ring 6, an air inlet hole 14 is formed in one end, close to the suction nozzle 1, of the side wall of the atomizer shell 10, an air inlet groove 15 is formed in one end, close to the suction nozzle 1, of the atomization core bracket 8, and the air inlet hole 14 communicate with the air pass groove 62 through the air inlet groove 15. An air pass hole 63 is formed in a position in the pressing ring 6, the position in the pressing ring 6 corresponds to one end, away from the suction nozzle 1, of the atomization piece 2, and the air pass hole 63 communicates the air pass groove 62 and the first hollow cavity I. The direction as shown by a solid arrow in FIG. 1 and the direction as shown by an arrow in FIG. 6 are flow directions of airflow.

The positive electrode of the heating body 4 penetrates through a first through hole 64 in the pressing ring 6 and is connected with one end of the power supply, and the negative electrode of the heating body 4 penetrates through a second through hole 65 in the in the pressing ring 6 and is connected with the other end of the power supply.

A depressed region 81 is formed in the outer side wall of the atomization core bracket 8.

A second hollow cavity II is formed between the atomization piece 2 and the washer 5.

A third hollow cavity III is formed between the pressing ring 6 and the inner side wall of the atomizer shell 10, and a fourth hollow cavity IV is formed between the atomization core and the inner side wall of the atomizer shell 10.

A tobacco tar bottle placing cavity 82 which places the tobacco tar bottle 7 is formed in one end, away from the suction nozzle 1, of the atomization core bracket 8.

The heating body 4 is in contact with a position, aligned to the central area of the atomization piece 2, of the atomization cotton 3.

The heating body 4 is a disc-shaped electric heating wire.

A wiring groove 83 is formed in the atomization core bracket 8. Wiring grooves 83 are also formed in the pressing ring 6.

A sealing pad 9 is arranged in the suction nozzle 1.

A tobacco tar injection opening 16 which injects tobacco tar into the tobacco tar bottle 7 is formed in a position, corresponding to the side edge of the tobacco tar bottle 7, on the atomizer shell 10, and a tobacco tar injection plug 17 penetrates through a sealing ring 18 to plug the tobacco tar injection opening 16. A tobacco tar bottle cover 19 is arranged on one side surface of the tobacco tar bottle 7, and a tobacco tar observation window 20 is formed in a position corresponding to the tobacco tar bottle cover 19 on the atomizer shell 10.

Embodiment 2

Figure 7:
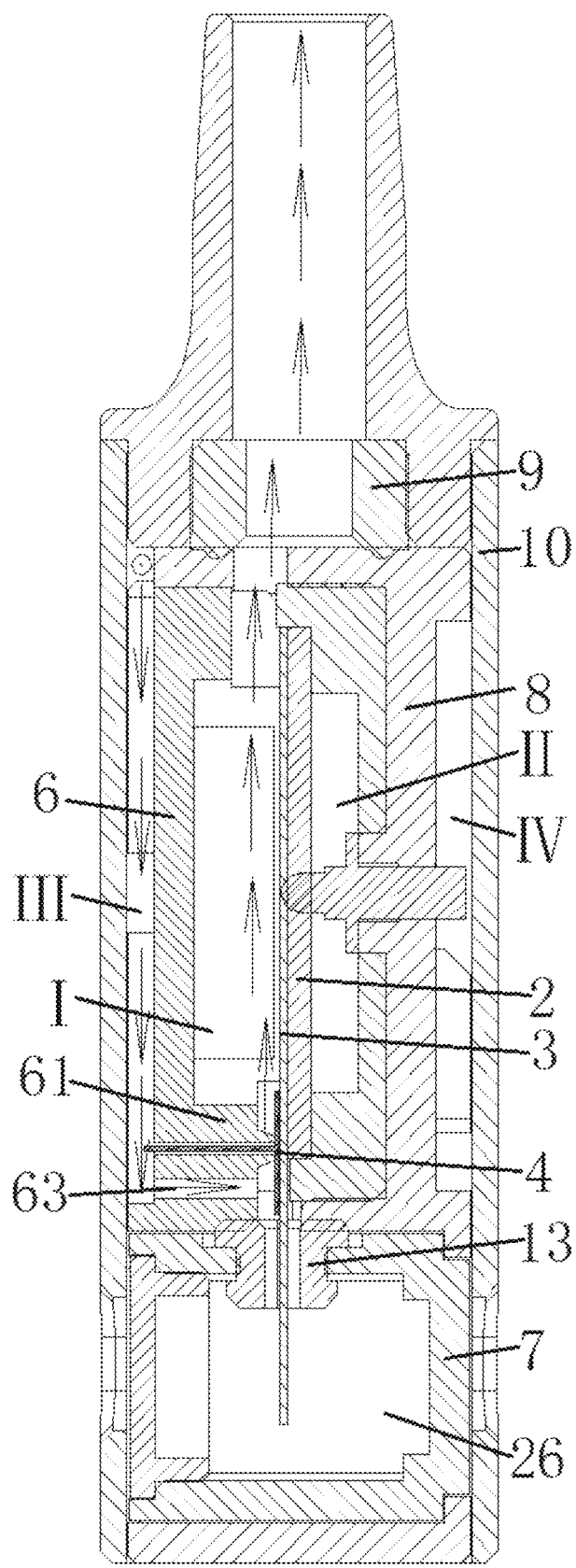
FIG. 7 is a front section view of an embodiment 2 of the present invention.

FIG. 7 shows the second embodiment of the present invention, the structure of the embodiment 2 is similar to that of the embodiment 1, the difference lies in that the heating body 4 is in contact with a position, close to a tobacco tar cup, of the atomization cotton 3, and the heating body 4 is an electric heating piece. The direction as shown by an arrow in FIG. 7 is flow direction of the airflow. The structure in the embodiment 2 which is the same as that in the embodiment 1 will not be repeated redundantly again, but it does not affect understanding and implementation of the present invention by those skilled in the art.

Embodiment 3

Figure 8:
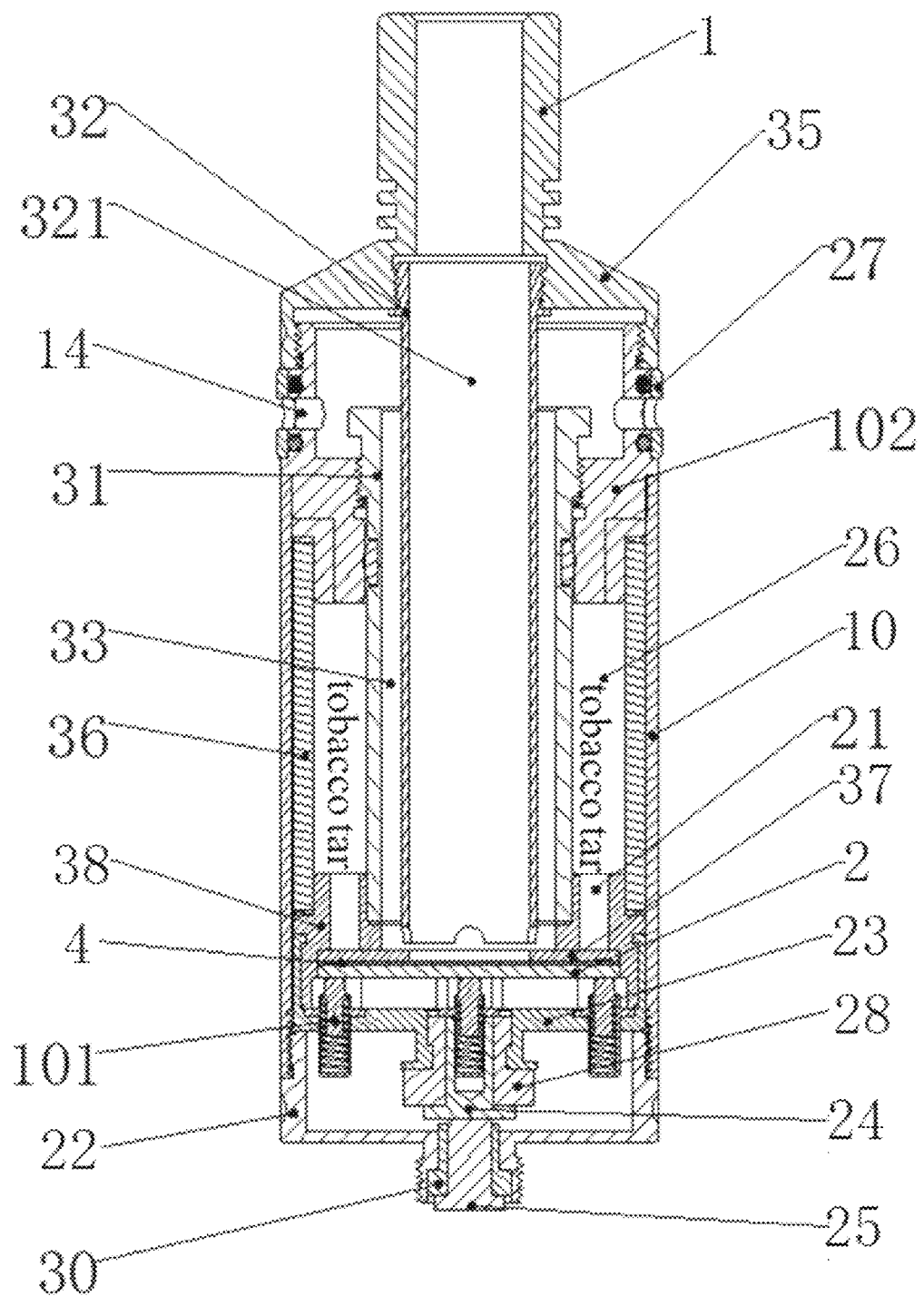
FIG. 8 is a structural schematic diagram of an embodiment 3 of the present invention.
Figure 9:
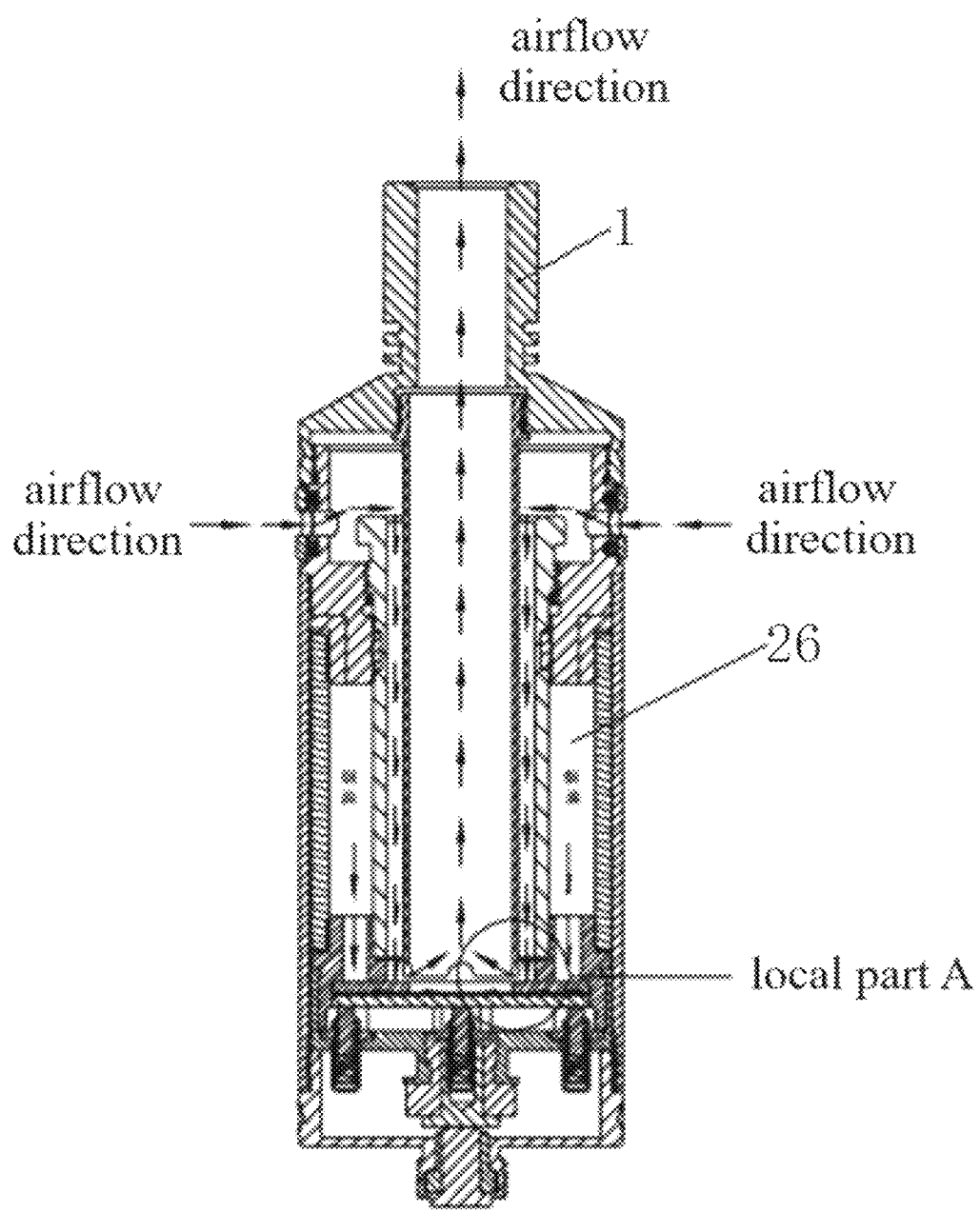
FIG. 9 is a schematic diagram of an airflow direction of the embodiment 3 of the present invention.
Figure 11:
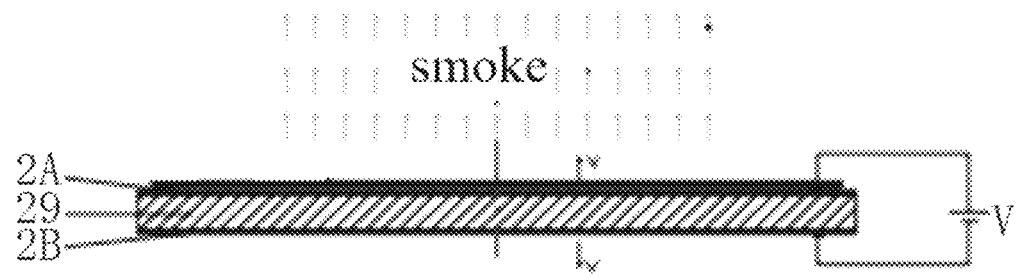
FIG. 11 is a structural schematic diagram of an atomization piece in FIG. 8.

As shown in FIG. 8, FIG. 9 and FIG. 11, an ultrasonic electronic cigarette atomizer in the embodiment 3 comprises an atomization piece 2 and a heating body 4; the atomization piece 2 comprises a piezoelectric ceramic layer 29; the upper surface and lower surface of the piezoelectric ceramic layer 29 are respectively in contact with a first conducting layer 2A (sliver layer) and a second conducting layer 2B (sliver layer); the first conducting layer 2A and the heating body 4 are in contact with the liquid guide structure which is used for guiding tobacco tar onto the heating body 4; the liquid guide structure communicates with a liquid storage cavity 26; the upper surface of the first conducting layer 2A communicates with an airflow passage; or conductors can be printed on two end surfaces of the piezoelectric ceramic layer to form the atomization piece, and the atomization piece is a solid atomization piece structure.

The atomization piece 2, the heating body 4 and the liquid storage cavity 26 are sequentially arranged along outflow direction of the atomized gas, so that the tobacco tar in the liquid storage cavity 26 can conveniently flow into the liquid guide structure under the action of its own gravity.

The airflow passage comprises an air inlet pipe 31 and an air outlet pipe 32 arranged in the air inlet pipe 31, an air inlet passage 33 is arranged between the inner wall of the air inlet pipe 31 and the outer wall of the air outlet pipe 32; the air inlet pipe 31 communicates with the air outlet pipe 32 through the air inlet passage 33; the bottom end (i.e., one end close to the atomization piece 2) of the air outlet pipe 32 communicates with the upper surface of the atomization piece 2; the air inlet pipe 31 and the top end (i.e., one end away from the atomization piece 2) of the air outlet pipe 32 are fixedly connected with a suction nozzle seat 35 and communicate with the suction nozzle 1 on the suction nozzle seat 35; air inlet holes 14 are formed in the suction nozzle seat 35; and the air inlet passage 33 communicates with the air inlet hole 14.

The bottom end of the air inlet pipe 31 abuts against the upper surface of the liquid guide structure through an adjusting mechanism which controls the tobacco tar throughput, and an air inlet notch 34 is formed in the bottom end of the air outlet pipe 32; an air outlet passage 321 is arranged in the air outlet pipe 32; and the air inlet passage 33 communicates with the air outlet passage 321 through the air inlet notch 34.

An adjusting device 27 (i.e., an air adjusting ring, an air adjusting hole is formed in a position, corresponding to the air inlet, of the air adjusting ring, the air adjusting ring is rotated in use to change the size of the communication part of the air adjusting hole and the outside, so the airflow volume can be adjusted, and when the air adjusting hole is overlapped with the air inlet, the air inlet volume is the maximum) which adjusts the airflow volume of the air inlet hole 14 is arranged on the suction nozzle seat 35.

Figure 10:
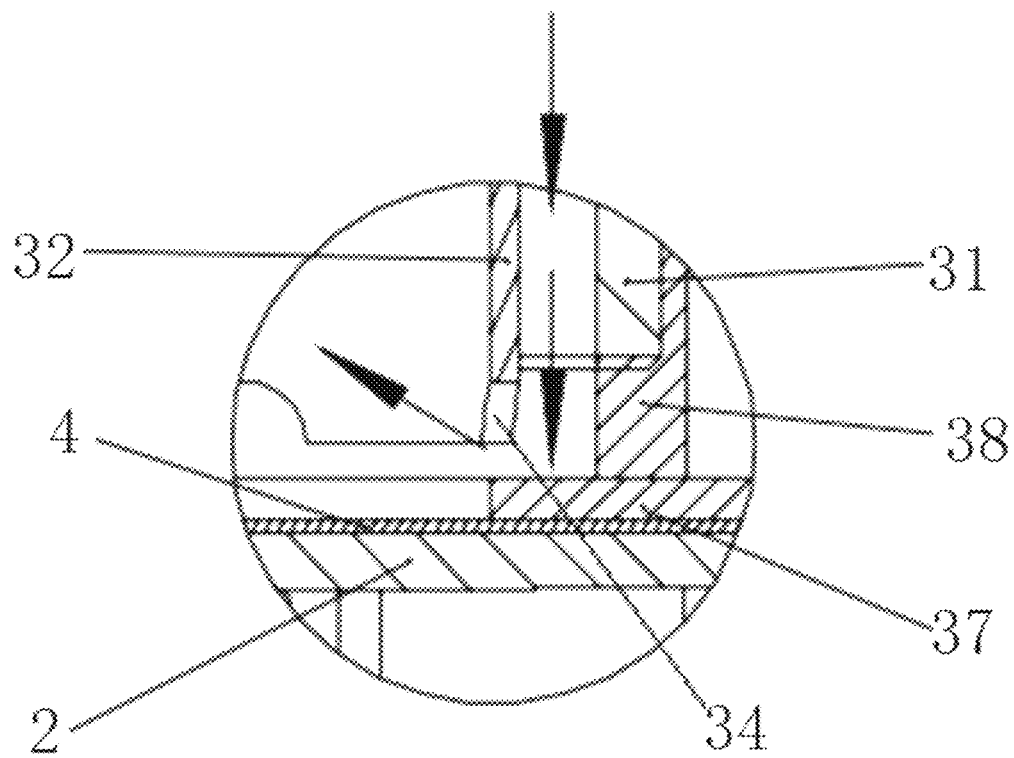
FIG. 10 is an enlarged view of a local part A of FIG. 9.

As shown in FIG. 8 and FIG. 10, the liquid guide structure is in contact with the upper surface (i.e., one surface close to the suction nozzle) of the heating body 4; and the bottom end of the air outlet pipe 32 abuts against the upper surface (i.e., the surface, away from the atomization piece, of the liquid guide structure) of the liquid guide structure, and the air inlet notch 34 is formed in the bottom end of the air outlet pipe 32. The air outlet passage 321 is arranged in the air outlet pipe 32; and the air inlet passage 33 communicates with the air outlet passage 321 through the air inlet notch 34.

As shown in FIG. 10, the interval between the bottom end of the air outlet pipe 32 and the upper surface of the atomization piece 2 is about 0.5-1.0 mm (the interval can be adjusted according to actual demands) so as to not only prevent that the air in the air inlet passage 33 cannot enter the air outlet passage 321 because it is blocked, but also prevent the smoke from entering the air inlet passage 33 to affect the taste of the smoke.

The liquid guide structure comprises porous material 37; a liquid supply hole 21 in the bottom end of the liquid storage cavity 26 is covered by or filled with the upper surface of the porous material 37; the porous material 37 and/or the atomization piece 2 is arranged in an elastic adjusting sleeve 38 (a silica gel sleeve can be used), and the outer wall of the upper part (i.e., one end, close to the liquid storage cavity 26, of the elastic adjusting sleeve 38) of the elastic adjusting sleeve 38 is hermetically connected with the inner wall of the bottom end (i.e., one end away from the suction nozzle) of the liquid storage cavity 26; and both of the liquid storage cavity 26 and the elastic adjusting sleeve 38 are arranged in the atomizer shell 10.

As shown in FIG. 8 and FIG. 10, the adjusting mechanism comprises the elastic adjusting sleeve 38 and atop seat 102; the upper end of the elastic adjusting sleeve 38 is arranged between the air inlet pipe 31 and the liquid storage cavity 26, and the bottom end of the air inlet pipe 31 is in contact with the elastic adjusting sleeve 38; at least one liquid supply hole 21 which communicates with the liquid guide structure is formed in the upper end of the elastic adjusting sleeve 38; the atomization piece 2, the heating body 4 and the liquid guide structure are all arranged in the inside of the lower end of the elastic adjusting sleeve 38; and the inner wall of the top seat 102 is in threaded connection with the air inlet pipe 31.

The liquid guide structure comprises the porous material 37; the liquid supply hole 21 is covered by or filled with the upper surface of the porous material 37; and both of the liquid storage cavity 26 and the elastic adjusting sleeve 38 are arranged in the atomizer shell 10, so that the inner structure of the atomizer is more compact, the leakage of tobacco tar is prevented, and the phenomenon that the atomization piece is stuck and cannot vibrate is prevented.

Figure 12:
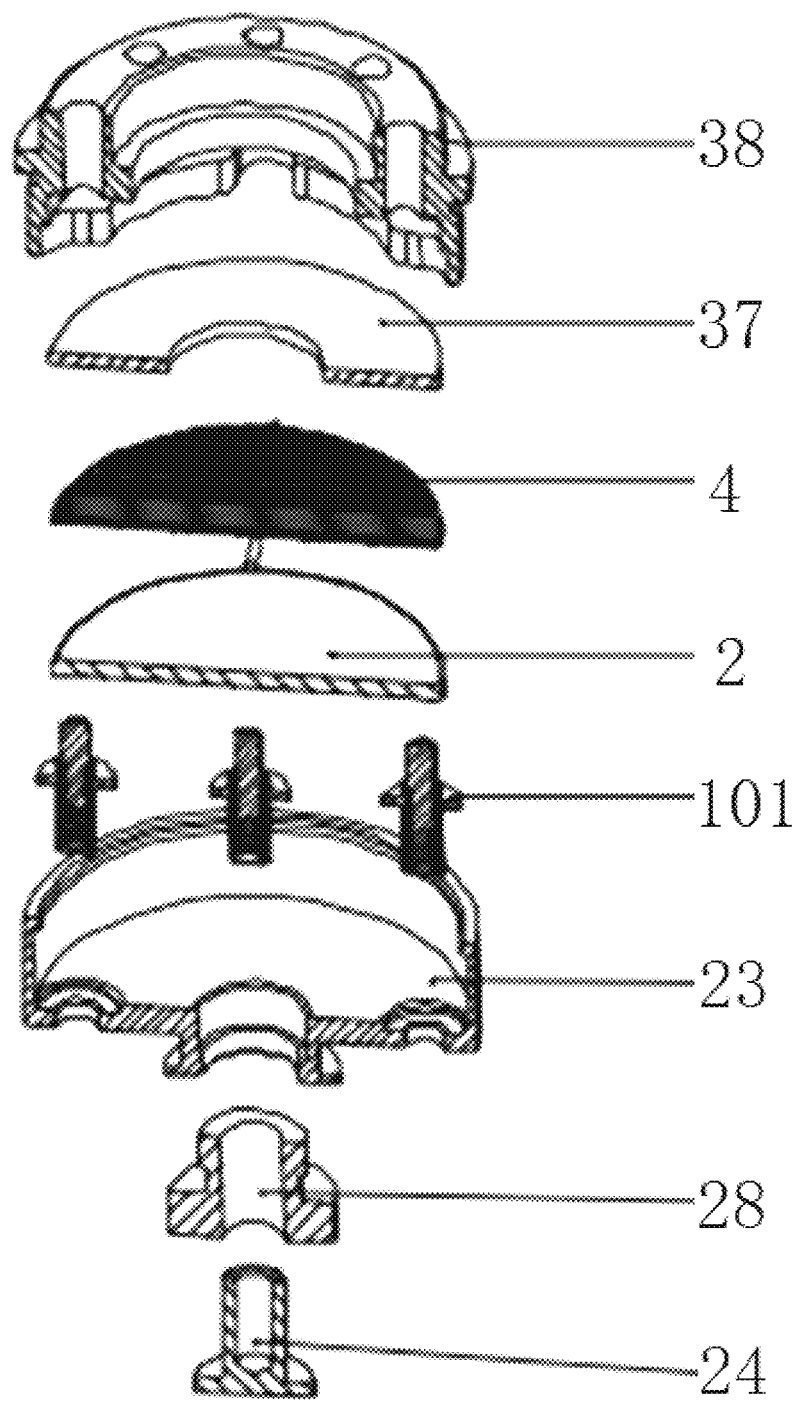
FIG. 12 is an explosive view of an atomization part in the embodiment 3 of the present invention.

As shown in FIG. 8 and FIG. 12, the lower surface of the atomization piece 2 is in contact with a plurality of elastic ejector pins 101; the elastic ejector pins 101 are fixedly connected with an atomization bottom seat 23; and the lower end of the elastic adjusting sleeve 38 is arranged in the atomization bottom seat 23. The elastic ejector pins 101 can ensure more stable and reliable internal electrical connection of the atomizer, compared with the electric conduction mode of electronic wires, the elastic ejector pins can prevent the high temperature produced by the atomization piece 2 at work from melting a bonding pad to cause drop of the electronic wires and produce an open circuit phenomenon.

The outer wall of the lower part (one end away from the liquid storage cavity 26) of the elastic adjusting sleeve 38 is in contact with the inner wall of the atomization bottom seat 23, the outer wall of the atomization bottom seat 23 is in contact with the inner wall of the atomizer shell 10, and an atomization electrode 24 insulated and isolated from the atomization bottom seat 23 (being insulated and isolated through an atomization insulating ring 28) is arranged in the atomization bottom seat 23; the atomization bottom seat 23 is fixedly connected with the top end (one end close to the atomization piece) of a bottom seat 22; the outer wall of the bottom seat 22 is in threaded connection with the inner wall of the atomizer shell 10; and an electrode ring insulated and isolated from the bottom seat 22 (being insulated and isolated through a bottom seat insulating ring 29) and in contact with the atomization electrode 24 is fixed in the bottom seat 22.

The elastic adjusting sleeve can be made of silica gel.

As shown in FIG. 12, the heating body 4 is a netlike heating wire, and the netlike heating wire is superposed on the upper surface of the atomization piece 2.

Figure 13:
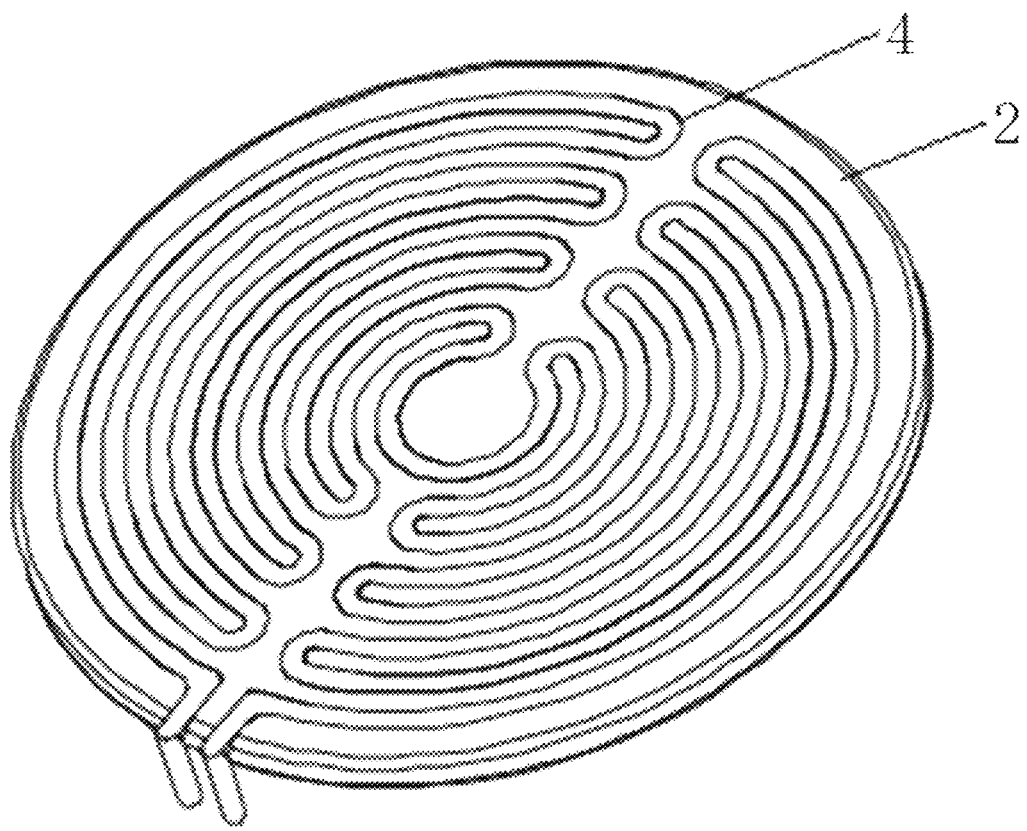
FIG. 13 is a structural schematic diagram of the second type of atomization piece and a heating body in the embodiment 3 of the present invention.

As shown in FIG. 13, the heating body of the present invention can also be embedded in the upper surface of the atomization piece 2, the heating wire is of snakelike-shaped structure and forms an integrated structure with the atomization piece, one end and the other end of the heating wire are led out from the periphery of the atomization piece and are respectively connected with the positive electrode and the negative electrode of a battery. The structure can increase the heating area, and improve the heating efficiency and the atomization efficiency, and the integrated structure makes the assembly simpler and more convenient.

Figure 14:
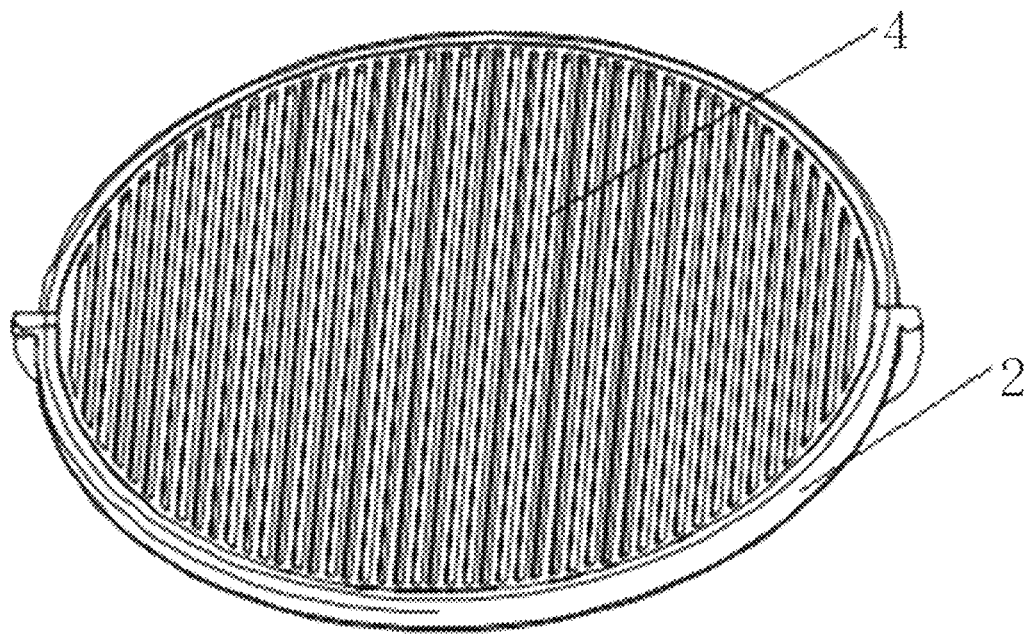
FIG. 14 is a structural schematic diagram of the third type of atomization piece and the heating body in the embodiment 3 of the present invention.

As shown in FIG. 14, the heating body is distributed in the form of a strip-shaped heating piece and is embedded in the atomization piece to form an integrated structure with the atomization piece, and one end and the other end of the heating piece are led out from the periphery of the atomization piece and are respectively connected with the positive electrode and the negative electrode of the battery.

Figure 15:
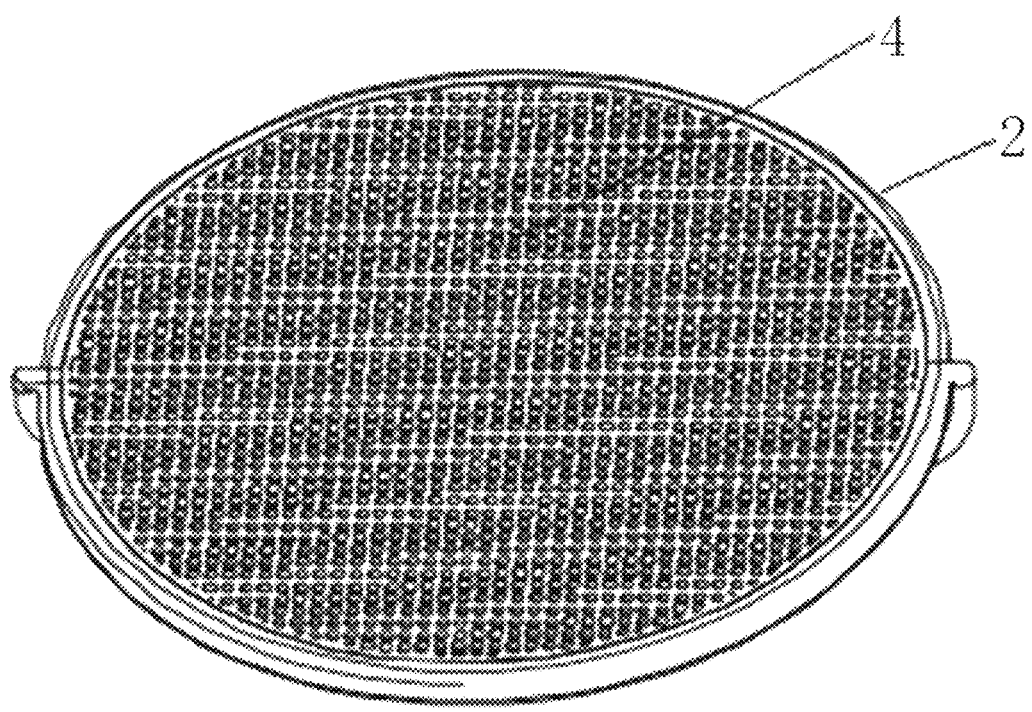
FIG. 15 is a structural schematic diagram of the third type of atomization piece and the heating body in the embodiment 3 of the present invention.

As shown in FIG. 15, the heating body is a netlike heating wire and is embedded in the atomization piece to form an integrated structure with the atomization piece, and one end and the other end of the heating piece are led out from the periphery of the atomization piece and are respectively connected with the positive electrode and the negative electrode of the battery.

As shown in FIG. 8, the liquid storage cavity 26 adopts a glass outer wall 36, and the inside of the top of the glass outer wall 36 is in contact with the outer wall of the top end of the air inlet pipe 31 through a silica gel ring, therefore the sealing property is good.

When a smoker smokes, the air enters the air inlet passage 33 from the air inlet hole 14 and enters the air outlet pipe 32 through the bottom of the air inlet passage 33, meanwhile the heating body 4 performs heating to heat the tobacco tar to a critical temperature, the atomization piece 2 oscillates to atomize the tobacco tar on its surface, and the atomized gas is mixed with the external air and is inhaled by the smoker after passing by the air outlet pipe 32.

Although the embodiments of the present invention have been described above in combination with the drawings, the present invention is not limited to the specific implementations described above, and the specific implementations described above are merely illustrative and are not restrictive, those of ordinary skill in the art can also make a lot of forms under the enlightenment of the present invention without departing from the purpose of the present invention or the protection scope of the claims, and all these forms fall within the protection scope of the present invention.

The invention claimed is:

1. An ultrasonic electronic cigarette atomizer, comprising an atomizer shell, wherein:
   an ultrasonic atomization piece and a liquid guide structure are arranged in the atomizer shell, the liquid guide structure communicates with a liquid storage cavity in the atomizer shell,
   a heating body is further arranged in the atomizer shell, both of the ultrasonic atomization piece and the heating body are in contact with the liquid guide structure, both of the heating body and an atomization surface of the ultrasonic atomization piece communicate with an airflow passage, and
   a positive electrode and a negative electrode of the heating body are respectively connected with one end and another end of a power supply.

2. The ultrasonic electronic cigarette atomizer of claim 1, wherein the liquid guide structure comprises atomization cotton in contact with one side surface of the ultrasonic atomization piece, both of the ultrasonic atomization piece and the atomization cotton being fixed on an atomization core bracket, the atomization cotton being clamped between the heating body and the ultrasonic atomization piece.

3. The ultrasonic electronic cigarette atomizer of claim 2, wherein one end of a side wall of the atomizer shell is connected with a suction nozzle, a washer and a pressing ring, which are detachably connected with each other, and are arranged in the atomization core bracket, and the ultrasonic atomization piece is arranged to be parallel to a length direction of an electronic cigarette, the ultrasonic atomization piece is fixed in the washer, one end of the atomization cotton is arranged between the washer and the pressing ring, and another end of the atomization cotton extends into a tobacco tar bottle, a projection which abuts against the heating body is arranged on the pressing ring, a first hollow cavity which communicates with the suction nozzle is formed between the pressing ring and the atomization cotton, an air pass groove which communicates with an outside and is parallel to the length direction of the electronic cigarette is formed in the side wall, away from the ultrasonic atomization piece, of the pressing ring, an air pass hole is formed in a position in the pressing ring, the position in the pressing ring corresponds to one end, away from the suction nozzle, of the ultrasonic atomization piece, and the air pass hole communicates the air pass groove and the first hollow cavity.

4. The ultrasonic electronic cigarette atomizer of claim 2, wherein a depressed region is formed in an outer side wall of the atomization core bracket.

5. The ultrasonic electronic cigarette atomizer of claim 3, wherein a second hollow cavity is formed between the ultrasonic atomization piece and the washer.

6. The ultrasonic electronic cigarette atomizer of claim 3, wherein a tobacco tar bottle placing cavity which places the tobacco tar bottle is formed in one end, away from the suction nozzle, of the atomization core bracket.

7. The ultrasonic electronic cigarette atomizer of claim 6, wherein the heating body is in contact with a first position, aligned to a central area of the ultrasonic atomization piece, of the atomization cotton, or the heating body is in contact with the atomization cotton at a second position, which is closer to a tobacco tar cup than the first position.

8. The ultrasonic electronic cigarette atomizer of claim 2, wherein the heating body is an electric heating piece or a disc-shaped electric heating wire.

9. The ultrasonic electronic cigarette atomizer of claim 2, wherein a wiring groove is formed in the atomization core bracket.

10. The ultrasonic electronic cigarette atomizer of claim 3, wherein a sealing pad is arranged in the suction nozzle.

* * * * *